United States Patent [19]

Tsuchiya et al.

[11] 4,396,763

[45] Aug. 2, 1983

[54] HIGH MOLECULAR POLYSACCHARIDE MPS-80

[75] Inventors: Fumiyasu Tsuchiya, Tokorozawa; Kyushichi Miyazawa, Hachioji; Michio Kanbe, Higashimurayama; Munehiro Oda, Tokyo; Naoyuki Ebisawa, Mitaka, all of Japan

[73] Assignee: Meiji Milk Products Company Limited, Tokyo, Japan

[21] Appl. No.: 322,183

[22] Filed: Nov. 17, 1981

[30] Foreign Application Priority Data

Jan. 14, 1981 [JP] Japan .............................. 56/563039
Jan. 14, 1981 [JP] Japan .............................. 56/563040

[51] Int. Cl.³ .......................... C07H 3/04; C08B 37/00
[52] U.S. Cl. .................................. 536/123; 424/180; 424/181; 536/1.1

[58] Field of Search .................. 536/1.1, 123; 424/180

[56] References Cited

U.S. PATENT DOCUMENTS 4,207,414  6/1980  Kasper ..................................... 536/1
4,229,440 10/1980  Murofushi et al. ..................... 536/1
4,324,887  4/1982  Kasper ..................................... 536/1

Primary Examiner—Johnnie R. Brown
Attorney, Agent, or Firm—Browdy & Neimark

[57] ABSTRACT

New high molecular polysaccharide MPS-80 was obtained by culturing high molecular polysaccharide MPS-80-producing bacteria belonging to genera Lactobacillus or Streptococcus. The new high molecular polysaccharide MPS-80 has an excellent anti-tumor effect, and it is expected for the utilization as anti-tumor agent.

1 Claim, 4 Drawing Figures

HIGH MOLECULAR POLYSACCHARIDE MPS-80

The present invention relates to new polysaccharide MPS-80 and a process for producing the same.

More particularly, the present invention relates to polysaccharide MPS-80 having a high viscosity and anti-tumor effect.

High molecular polysaccharide MPS-80 of the present invention can be obtained by culturing high molecular polysaccharide MPS-80-producing bacteria belonging to the group consisting of genera Lactobacillus and Streptococcus. As concrete examples of the high molecular polysaccharide MPS-80-producing bacteria, there may be mentioned Lactobacillus Jugurti No. 851 "FERM BP-66(FERM-P No. 5851)" and Streptococcus thermophilus No. 127 "FERM BP-65(FERM-P No. 5850)" deposited in the Fermentation Research Institute, Agency of Industrial Science and Technology. They are used effectively.

The present invention relates to high molecular polysaccharide MPS-80 and a process for producing the same.

High molecular polysaccharide MPS-80 can be obtained by culturing high molecular polysaccharide MPS-80-producing bacteria and separating the same from the liquid fraction and the bacterial fraction of the culture mixture.

As the culture medium, any culture medium of unlimited composition may be used. Among them, a lactic acid bacteria culture medium containing skim milk or whey and so forth is preferred.

As for culture conditions, satisfactory results can be obtained by, for example, static culture at 20°–45° C. The culture may be effected under conditions which allow the high molecular polysaccharide MPS-80-producing bacteria to grow, thereby producing the high molecular polysaccharide MPS-80.

The culture mixture of the high molecular polysaccharide MPS-80-producing bacteria is divided by the centrifugation into liquid fraction and bacterial fraction. From those fractions, the high molecular polysaccharide MPS-80 having anti-tumor effects is collected. The high molecular polysaccharide MPS-80 may be collected from the liquid fractin by an ordinary method such as gel filtration, ion exchange chromatography, salting out, solvent fractionation and dialysis, etc. Those methods may be employed alone or combined suitably. The high molecular polysaccharide MPS-80 may be collected from the bacterial fraction by, for example, extracting the same with water and then treating the extract in the same manner as in the above method of collecting from the liquid fraction.

In the process of the present invention, generally, the high molecular polysaccharide MPS-80-producing bacteria are cultured in a whey medium and the culture mixture is subjected to the centrifugation to obtain a supernatant liquid.

Then, an organic solvent is added to the supernatant liquid to form precipitate.

On the other hand, the bacterial fraction obtained by the centrifugation is subjected to the extraction with water and then the extract is subjected to the centrifugation to obtain an extracted, supernatant liquid.

An organic solvent is added to the supernatant liquid to obtain precipitate.

Both precipitates obtained as above are dissolved in water and an organic solvent is added thereto to effect the reprecipitation. The precipitates are dissolved in a suitable buffer solution and charged in an ion exchanger which has been buffered sufficiently with the same buffer solution as above. Then, the same buffer solution is passed through the ion exchanger. A liquid containing the high molecular polysaccharide not adsorbed on the ion exchanger is recovered and dialyzed using ion-exchanged water. The dialyzed solution is freeze-dired to obtain purified high molecular polysaccharide MPS-80.

Thus obtained high molecular polysaccharide MPS-80 has an excellent anti-tumor effect and is useful as anti-tumor agent, and its high viscosity is useful as thickening agent.

Physicochemical properties of the high molecular polysaccharide MPS-80 of the present invention are as follows:

(1) Elementary analysis:
C: 42.2%
H: 6.9%
O: 50.4%

(2) Molecular weight:

(i) Molecular weight determined by ultrafiltration method:

The results of ultrafiltration by means of Sepharose 2B are shown in FIG. 1.

This polysaccharide is fractionated near the void volume under conditions comprising 2.5×40.5 cm column size, 5 g fraction, 2.5 mg (1 ml) sample loaded and 0.05 M phosphate buffer solution (pH 6.0) used as developer.

(ii) Molecular weight determined by ultracentrifugation:

A sample is dissolved in 0.2 M phosphate buffer solution (pH 7.3) and the resulting solution having a concentration of 0.1% is subjected to the ultracentrifugation (preset rotation rate: 51,200 RPM) to obtain a sedimentation constant of 7.98S (S: Svedberg unit). (The sedimentation pattern was single.)

(3) Melting point (decomposition point):
This polysaccharide begins to discolor at around 262° C. and is blackened at 263°–264° C.

(4) Specific rotatory power:

$$[\alpha]_D^{18} = +33.2 \ (C=0.5\%)$$

(5) Ultraviolet ray absorption spectrum:
See FIG. 2.

(6) Infrared ray absorption spectrum:
See FIG. 3.

(7) Solubilities in solvents:
Soluble in water but insoluble in methanol, ethanol, acetone and ether.

(8) Color reactions:
(i) Molisch reaction: +
(ii) Anthrone reaction: +
(iii) Cysteine sulfuric acid reaction: +
(iv) Aniline hydrochloric acid reaction: −
(v) Carbazole sulfuric acid reaction: −
(vi) Elson-Morgan reaction: −
(vii) Biuret reaction: −

(9) Basicity, acidity or neutrality:
0.1–0.5% aqueous solution of this polysaccharide has a neutral pH.

(10) Color:
Freeze-dried polysaccharide is in the form of white fibers.

(11) Saccharide constituting the polysaccharide:

Saccharide constituting the polysaccharide was examined by GLC using 5% SE-52 (2 m column) as follows:

Column heating condition was 150° C.–230° C. (3° C./min.).

The sample was hydrolyzed with 2 N-$H_2SO_4$ in boiling water for 4 hours, then neutralized with barium carbonate and subject to the filtration. The filtrate was demineralized with Amberlite IRA-410 and Amberlite IR-120B, concentrated to dryness and subjected to TMS treatment followed by GLC. As a result, glucose and galactose were observed as the saccharide constituting the polysaccharide.

(12) Proportion of saccharide constituting the polysaccharide:

The sample was hydrolyzed with 2 N-$H_2SO_4$ in boiling water for 4 hours, neutralized with barium carbonate and subjected to the filtration. The filtrate was examined to determine a proportion of saccharide constituting the polysaccharide. Ratio of glucose to galactose was 2.2–1.9 to 1.

(13) $C^{13}$-NMR Spectrum (in $D_2O$, TMS standard) (ppm):

The results are shown in FIG. 4.

(14) Decomposition with enzymes:

This polysaccharide was dissolved in 0.05 M acetate buffer solution and subjected to the reaction with various enzymes. The decomposition by the enzymes was judged from increase in amount of reduced sugar by Somogyi-Nelson method.

Enzymes used and reaction conditions:

| | | |
|---|---|---|
| a. | α-Amylase (a product of Boehringer) | |
| | pH 5.9, 37° C. 4 hrs. | |
| b. | β-Amylase (a product of Boehringer) | |
| | pH 4.8, 30° C., 4 hrs. | |
| c. | β-Galactosidase (a product of Boehringer) | |
| | pH 4.8, 30° C., 4 hrs. | |
| d. | Amyloglucosidase (a product of Boehringer) | |
| | pH 4.8, 30° C., 4 hrs. | |
| e | α-Galactosidase (a product of Boehringer) | |
| | pH 4.8, 30° C., 4 hrs. | |

No increase in amount of reduced sugar was recognized at all under above conditions a through e.

(15) $LD_{50}$ ddY 5 w ♀ mice (average body weight: 21.3 g; each group consisted of 7 mice) were used. A sample solution in physiological saline was administered intraperitoneally once in various amounts to the mice and they were observed for 10 days to determine $LD_{50}$. As a result, $LD_{50}$ was not less than 200 mg/Kg-body weight.

The following examples and tests will further illustrate the present invention:

EXAMPLE 1

Lactobacillus Jugurti No. 851 "FERM BP-66(FERM-P No. 5851)" was inoculated into 10 liters of a whey medium (10% w/v whey powder +0.5% w/v beer yeast extract) and the static culture was effected at 37° C. for 24 hours. After completion of the culture, the culture mixture was centrifuged (10,000 rpm, 15 min.) to obtain 9.2 liters of a supernatant culture liquid. 99.5% Ethyl alcohol was added to the supernatant liquid in such an amount that the final concentration thereof would be 35% (v/v). A precipitate formed by this operation was centrifuged (10,000 rpm, 5 min.) to obtain 1.2 g of the precipitate.

Ion exchanged water was added to the precipitate to obtain a solution. An insoluble matter was removed from the solution by centrifugation (10,000 rpm, 15 min.). This treatment was repeated three times in total to obtain 800 mg of a roughly purified product.

The roughly purified product obtained as above was dissolved in 0.05 M phosphate buffer solution (pH 6.0) and the solution was introduced in a column charged with diethylaminoethyl cellulose (DEAE-cellulose) sufficiently buffered with the same buffer solution. The buffer solution was passed through the column and then the solution containing a substance not adsorbed on DEAE-cellulose was collected. The solution containing the non-adsorbed substance was freeze-dried, dissolved in ion-exchanged water and dialyzed by means of a dialysis tube using ion exchanged water at 10° C. for four days. After completion of the dialysis, the solution thus treated was freeze-dried to obtain 500 mg of a freeze-dried sample of high molecular polysaccharide MPS-80.

EXAMPLE 2

0.5 w/v% of beer yeast extract was added to 10 liters of 10 w/v% whey powder solution to obtain a culture medium.

Streptococcus thermophilus No. 127 "FERM BP-65(FERM-P No. 5850)" was inoculated into this medium and the static culture was effected at 37° C. for 20 hours. After completion of the culture, the culture mixture was centrifuged (10,000 rpm, 15 min.) to obtain 9 liters of a supernatant culture liquid. 99.5% Ethyl alcohol was added to the supernatant liquid in such an amount that the final concentration thereof would be 50 v/v%. By the centrifugation, (10,000 rpm, 5 min.) 1.7 g of a precipitate was obtained.

Ion exchanged water was added to the precipitate to obtain a solution. An insoluble matter was removed from the solution by centrifugation (10,000 rpm, 15 min.).

This treatment was repeated three times in total to obtain 1.2 g of a roughly purified product.

The roughly purified product obtained as above was dissolved in 0.05 M phosphate buffer solution (pH 6.0) and the solution was introduced in a column charged with diethylaminoethyl cellulose (DEAE-cellulose) sufficiently buffered with the same buffer solution.

The buffer solution was passed through the column and then the solution containing a substance not adsorbed on DEAE-cellulose was collected. The solution containing the non-adsorbed substance was freeze-dried, dissolved in ion-exchanged water and dialyzed by means of a dialysis tube using ion exchanged water at 10° C. for four days. After completion of the dialysis, the solution thus treated was freeze-dried to obtain 800 mg of a freeze-dried sample of high molecular polysaccharide MPS-80.

After column chromatography with Sepharose 2B and ultracentrifugal analysis, it was revealed that the above two samples were the same, single substance. When the sample was dissolved in water, a colorless, transparent solution was obtained.

TEST EXAMPLE 1

Effects on ascites Ehrlich carcinoma:

ddY Female mice (8 weeks old) were used. Each group consisted of 7 mice. $1 \times 10^5$ Ehrlich ascites tumor cells which had been subjected to the successive cultivation in ddY mice for one week were inoculated intraperitoneally. From the next day, physiological saline was administered to a control group and a solution of the high molecular polysaccharide MPS-80 obtained in Example 1 in physiological saline was administered to the test group intraperitoneally for 9 days continuously. The dosages were 15 mg/Kg/day and 60 mg/Kg/day.

The effects of the high molecular polysaccharide MPS-80 on ascites Ehrlich carcinoma were judged from degree of prolongation of life as compared with the control group.

The results are shown in Table 1.

TABLE 1

| Dosage (mg/Kg/day) | Intermediate Survival Time (day) | Degree of Prolongation of Life (%) | Number of Survivors after 60 Days |
|---|---|---|---|
| Control | 28 | 100 | 0/7 |
| 15 | 28 | 100 | 3/7 |
| 60 | <60 | <214 | 5/7 |

From the results given in Table 1, it is understood that high molecular polysaccharide MPS-80 exhibited a strong anti-tumor effect on ascites Ehrlich carcinoma.

TEST EXAMPLE 2

Effects on ascites Ehrlich carcinoma:

ddY Female mice (8 weeks old) were used. Each group consisted of 7 mice. $1 \times 10^5$ Ehrlich ascites tumor cells which had been subjected to the successive cultivation using ddY mice for one week were inoculated intraperitoneally. On that day, the intraperitoneal administration of physiological saline to a control group and a solution of the high molecular polysaccharide MPS-80 obtained in Example 2 in physiological saline to the test group was begun. The administration was continued for three days. The dosages were 12.5 mg/Kg/day, 25.0 mg/Kg/day and 50 mg/Kg/day.

The results are shown in Table 2.

TABLE 2

| Dosage (mg/Kg/day) | Intermediate survival time (day) | Degree of prolongation of life (%) | Number of survivors after 60 days |
|---|---|---|---|
| Control | 29 | 100 | 0/7 |
| 12.5 | 33 | 114 | 1/7 |
| 25.0 | 39 | 134 | 3/7 |
| 50.0 | 29 | 124 | 2/7 |

From the results shown in Table 2, it is understood that high molecular polysaccharide MPS-80 exhibited its effect with respect to the number of survivors after 60 days, though no remarkable effect on the degree of prolongation of life was recognized.

TEST EXAMPLE 3

Effects on subcutaneously implanted Ehrlich carcinoma:

ddY Female mice (8 weeks old) were used. Each group consisted of 8 mice. $1 \times 10^6$ Ehrlich ascites tumor cells which had been subjected to the successive cultivation using ddY mice for one week were implanted subcutaneously into the mice. From the next day, physiological saline was administered to a control group and a solution of the high molecular polysaccharide MPS-80 obtained in Example 1 in physiological saline was administered to the test group intraperitoneally for 8 days continuously. The dosages were 12.5 mg/Kg/day and 25.0 mg/Kg/day.

The effects of high molecular polysaccharide MPS-80 on subcutaneously implanted Ehrlich carcinoma were judged from number of the mice in which solid tumor regressed completely.

The results are shown in Table 3.

TABLE 3

| Dosage (mg/Kg/day) | Number of mice having solid tumor regressed 50 days after the transplantation |
|---|---|
| Control | 0/8 |
| 12.5 | 3/8 |
| 25.0 | 4/8 |

From the results shown in Table 3, it is understood that high molecular polysaccharide MPS-80 exhibited a remarkbble effects on subcutaneouly implanted Ehrlich carcinoma

TEST EXAMPLE 4

Effects on ascites Sarcoma-180:

ddY Female mice (8 weeks old) were used. Each group consisted of 5 mice. $1 \times 10^5$ Sarcoma 180 ascites tumor cells which had been subjected to the successive cultivation using ddY mice for one week were inoculated intraperitoneally. From the next day, physiological saline was administered to a control group and a solution of high molecular polysaccharide MPS-80 obtained in Example 1 in physiological saline was to the test group introperitoneally for 9 days continuously. The dosages were 12.5 mg/Kg/day, 25.0 mg/Kg/day and 50 mg/Kg/day. The effects of the high molecular polysaccharide MPS-80 on ascites Sarcoma-180 were judged from degree of prolongation of life as compared with the control group.

The results are shown in Table 4.

TABLE 4

| Dosage (mg/Kg/day) | Intermediate survival time (day) | Degree of prolongation of life (%) | Number of survivors after 60 days |
|---|---|---|---|
| Control | 23 | 100 | 0/5 |
| 12.5 | 24 | 104 | 2/5 |
| 25.0 | <60 | <261 | 3/5 |
| 50.0 | 44 | 191 | 2/5 |

From the results given in Table 4, it is understood that high molecular polysaccharide MPS-80 exhibited a strong anti-tumor effect on ascites Sarcoma-180.

TEST EXAMPLE 5

Effects on lymphocytic leukemia P-388:

$CDF_1$ Male mice (6 weeks old) were used. Each group consisted of 8 mice. $5 \times 10^3$ P-388 cells which had been subjected to the successive cultivation using DBA mice for one week were transplanted intraperitoneally. The effects were examined using a combination of Mitomycin C with high molecular polysaccharide MPS-80 obtained in Example 1.

On the day subsequent to the transplantation, the intraperitoneal administration of physiological saline to the control group was begun. The administration was continued for 10 days. Mitomycin C (1 mg/Kg) was administered only once to a group of only Mitomycin C administration. To the test group in which both Mitomycin C and high molecular polysaccharide MPS-80 are used, Mitomycin C (1 mg/Kg) was administered to the mice only once on the day subsequent to the transplantation and then high molecular polysaccharide MPS-80 was given intraperitoneally from the day subsequent to the Mitomycin C administration continuously for 9 days. The dosages of high molecular polysaccharide MPS-80 were 12.5 mg/Kg/day, 25.0 mg/Kg/day, 50.0 mg/Kg/day and 77.5 mg/Kg/day.

The effects obtained by the use of high molecular polysaccharide MPS-80 in combination with Mitomycin C were judged from degree of prolongation of life and number of survivors after 70 days.

The results are shown in Table 5.

TABLE 5

| Dosage (mg/Kg/day) | | Intermediate survival time (day) | Degree of prolongation of life (%) | Number of survivors after 70 days |
|---|---|---|---|---|
| Control | | 14.0 | 100 | 0/8 |
| Mitomycin C 1 mg | | 18.0 | 129 | 0/8 |
| Mitomycin C 1 mg | 12.5 | 21.0 | 150 | 0/8 |
| + | 25.0 | 19.5 | 139 | 0/8 |
| High molecular | 50.0 | 20.5 | 146 | 0/8 |
| polysaccharide | 77.5 | 21.5 | 154 | 2/8 |
| MPS-80 | | | | |

From the results shown in Table 5, it is understood that degrees of prolongation of life and numbers of survivors after 70 days indicate the effects obtained by the combination of high molecular polysaccharide MPS-80 with Mitomycin C.

Figure 1:
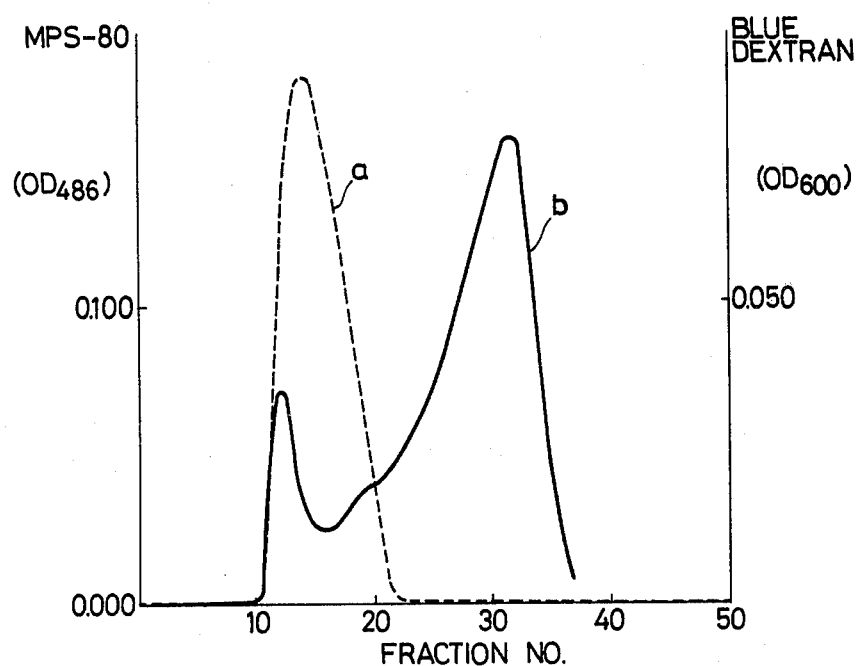
FIG. 1 is a development chart of high molecular polysaccharide MPS-80 according to ultrafiltration wherein a represents high molecular polysaccharide MPS-80 and b represents Blue Dextran.

What is claimed is:

1. High molecular polysaccharide MPS-80 having the following physicochemical properties:
   (1) elementary analysis:
      C: 42.2%
      H: 6.9%
      O: 50.4%
   (2) molecular weight:
      (i) molecular weight determined by ultrafiltration method by means of Sepharose 2B as shown in FIG. 1;
      said polysaccharide is fractionated near the void volume under conditions comprising 2.5×40.5 cm column size, 5 g fraction, 2.5 mg (1 ml) sample loaded and 0.05 M phosphate buffer solutin (pH 6.0) used as developer;
      (ii) molecular weight determined by ultracentrifugation wherein
   a sample is dissolved in 0.2 M phosphate buffer solution (pH 7.3) and the resulting solution having a concentration of 0.1% is subjected to the ultracentrifugation (preset rotation rate: 51,200 RPM) to obtain a sedimentation constant of 7.98S (S: Svedberg unit), the sedimentation pattern being single;
   (3) melting point (decomposition point):
      said polysaccharide begins to discolor at around 262° C. and is blackened at 263°–264° C.
   (4) specific rotatory power:

$[\alpha]_D^{18} = +33.2$ (C=0.5%)

Figure 2:
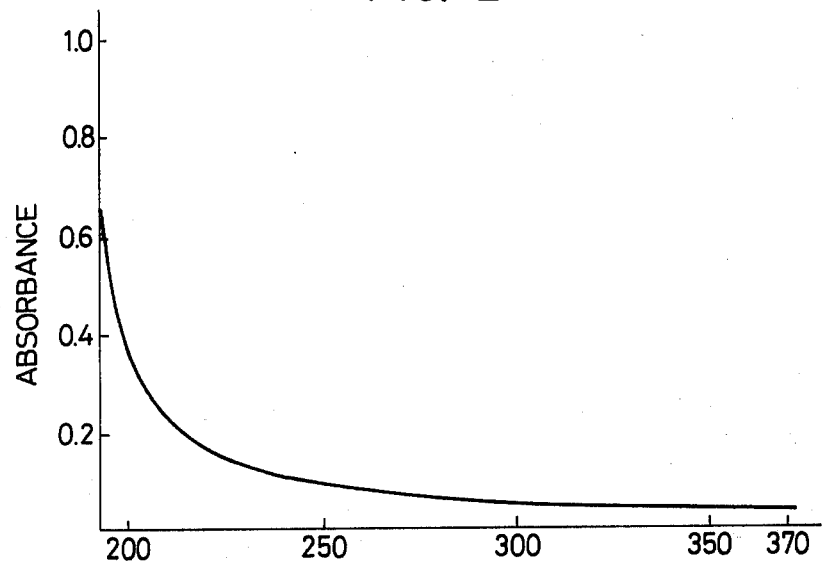
FIG. 2 shows U.V absorption spectrum of high molecular polysaccharide MPS-80.
Figure 3:
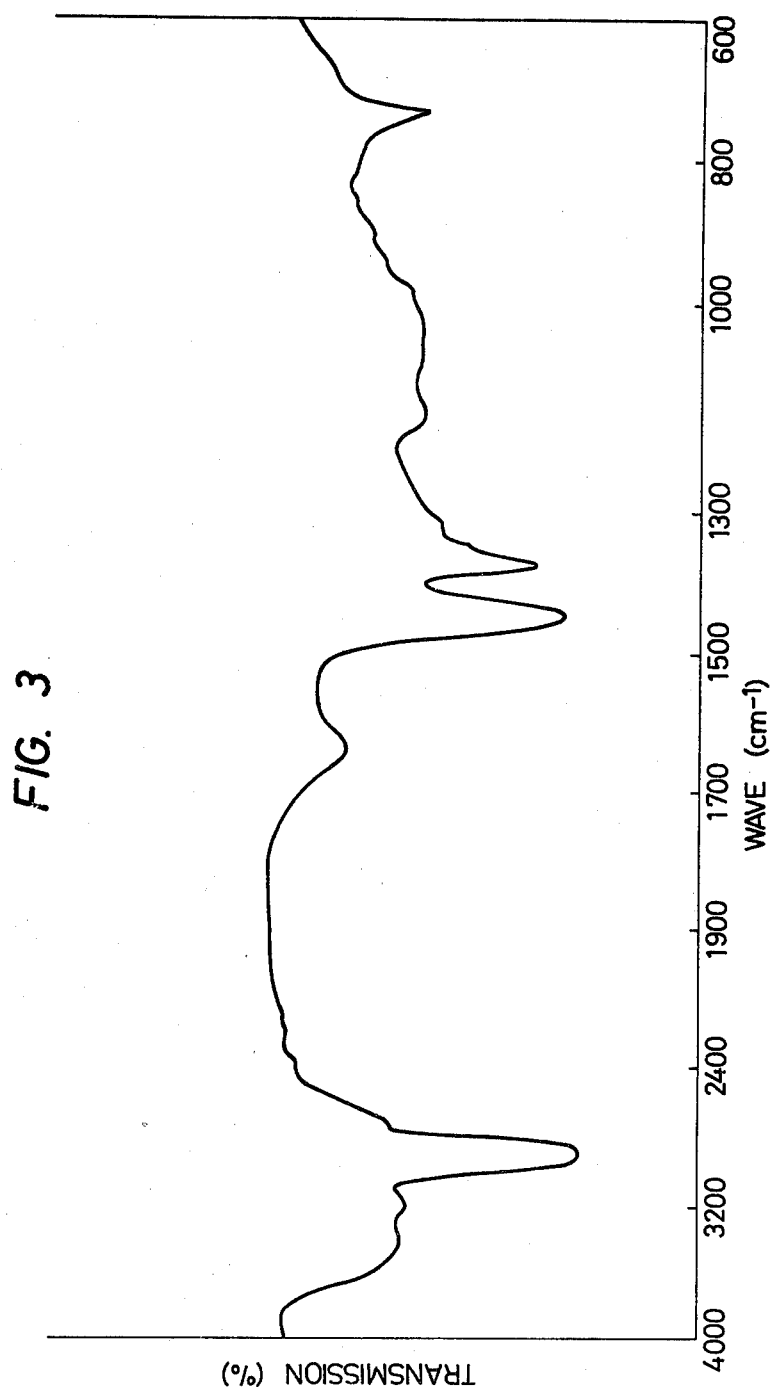
FIG. 3 shows infrared absorption spectrum of the same.
Figure 4:
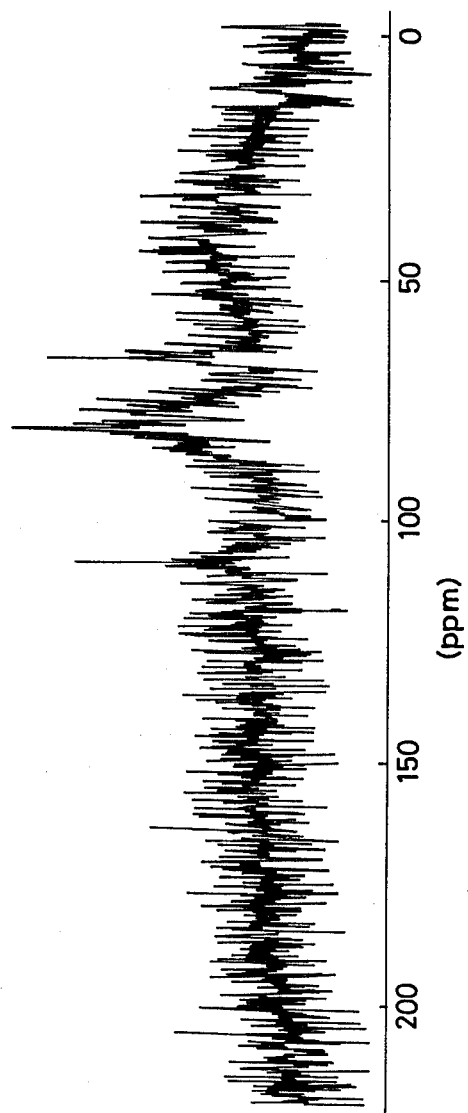
FIG. 4 shows $C^{13}$-NMR spectrum of the same.

(5) ultraviolet ray absorption spectrum:
      as shown in FIG. 2.
   (6) infrared ray absorption spectrum:
      as shown in FIG. 3.
   (7) solubilities in solvents:
      soluble in water but insoluble in methanol, ethanol, acetone and ether;
   (8) color reactions:
      (i) Molisch reaction: +
      (ii) Anthrone reaction: +
      (iii) Cysteine sulfuric acid reaction: +
      (iv) Aniline hydrochloric acid reaction: −
      (v) Carbazole sulfuric acid reaction: −
      (vi) Elson-Morgan reaction: −
      (vii) Biuret reaction: −
   (9) basicity, acidity or neutrality:
      0.1–0.5% aqueous solution of said polysaccharide has a neutral pH;
   (10) color:
      freeze-dried polysaccharide is in the form of white fibers;
   (11) saccharide constituting the polysaccharide are glucose and galactose determined by examining said polysaccharide by GLC using 5% SE-52 (2 m column) as follows:
      the sample was hydrolyzed with 2 N-$H_2SO_4$ in boiling water for 4 hours, then neutralized with barium carbonate and subjected to the filtration; the filtrate was demineralized with Amberlite IRA-410 and Amberlite IR-120B, concentrated to dryness and subjected to TMS treatment followed by GLC;
   (12) proportion of saccharide constituting the polysaccharide:
      a sample of said polysaccharide was hydrolyzed with 2N-$H_2SO_4$ in boiling water for 4 hours, neutralized with barium carbonate and subjected to filtration; the filtrate was examined to determine a proportion of saccharide constituting the polysaccharide by enzyme method; the ratio of glucose to galactose was 2.2–1.9 to 1;
   (13) $C^{13}$-NMR Spectrum (in $D_2O$, TMS standard) (ppm):
      as shown in FIG. 4;
   (14) decomposition with enzymes:
      said polysaccharide was dissolved in 0.05 M acetate buffer solution and subjected to reaction with various enzymes; the decomposition by the enzymes was judged from increase in amount of reduced sugar by Somogyi-Nelson method; Enzymes used and reaction conditions:

| | | |
|---|---|---|
| a. | Amylase (a product of Boehringer) | pH 5.9, 37° C., 4 hrs. |
| b. | Amylase (a product of Boehringer) | pH 4.8, 30° C., 4 hrs. |
| c. | Galactosidase (a product of Boehringer) | pH 4.8, 30° C., 4 hrs. |
| d. | Amyloglucosidase (a product of Boehringer) | pH 4.8, 30° C., 4 hrs. |
| e. | Galactosidase (a product of Boehringer) | pH 4.8, 30° C., 4 hrs. | no increase in amount of reduced sugar was recognized at all under above conditions a through e;
   (15) $LD_{50}$
      ddY w ♀ mice (average body weight: 21.3 g; each group consisted of 7 mice) were used; a sample solution in physiological saline was administered intraperitoneally once in various amounts to the mice and they were observed for 10 days to determine $LD_{50}$;

as a result, $LD_{50}$ was not less than 200 mg/Kg-body weight; and

(16) MPS-80 is produced by cultivating a member selected from the group consisting of Lactobacillus Jugurti No. 851, FERM BP-66 and Streptococcus thermophilus No. 127, FERM BP-65.

* * * * *